United States Patent [19]

Theller

[11] Patent Number: 5,331,858

[45] Date of Patent: Jul. 26, 1994

[54] HOT TACK TESTER

[75] Inventor: Hutton W. Theller, Petaluma, Calif.

[73] Assignee: H. W. Theller Inc., Petaluma, Calif.

[21] Appl. No.: 980,853

[22] Filed: Nov. 24, 1992

[51] Int. Cl.$^5$ ............................................. G01N 19/04
[52] U.S. Cl. ..................................................... 73/827
[58] Field of Search ................ 73/826, 827, 834, 835, 73/837, 150 A, 827; 374/49, 50

[56] References Cited

U.S. PATENT DOCUMENTS

| | | | |
|---|---|---|---|
| 2,377,869 | 6/1945 | Elliott | 73/826 |
| 2,834,205 | 5/1958 | Pickup | 73/150 A |
| 3,580,065 | 5/1971 | Strittmater | 73/150 |
| 3,850,033 | 11/1974 | Schmitt | 73/150 |

FOREIGN PATENT DOCUMENTS 142756 7/1980 German Democratic Rep. .
1259157 9/1986 U.S.S.R. .

OTHER PUBLICATIONS

Topwave DTC Hot Track Tester Brochure obtained from display booth at a trade show prior to Nov. 1991 in U.S. Date and place of publication unknown.
DTC Hot Tack Tester Operation Instructions provided to purchaser of a DTC Hot Tack Tester (duPont) in U.S. prior to Nov. 1991. Date and place of publication unknown.

*Primary Examiner*—Robert Raevis
*Attorney, Agent, or Firm*—Corwin R. Horton

[57] ABSTRACT

A procedure and apparatus for testing the hot tack properties of heat sealable flexible packaging materials. A portion of a test strip of heat sealable material is lapped and a segment of this portion heat sealed together. Upon completion of the heat seal the unsealed ends of the test strip are pulled apart at a prescribed constant rate to gradually delaminate the heat seal while the heat seal is cooled at a prescribed rate. Force required to delaminate the seal is continuously recorded as a function of time as the heat seal cools, thus providing data on seal strength for a full range of temperatures of the heat seal as it cools over time. In the apparatus a threading bar intercepts the strip intermediate its ends and pulls a portion through the opening between opposed dies of a heat sealer and in doing so laps the portion of the strip pulled through the opening. The test strip is then liberated from the threading bar during or following heat sealing of the lapped portion, as by cutting the strip at the threader.

13 Claims, 9 Drawing Sheets

HOT TACK TESTER

BACKGROUND OF THE INVENTION

This invention relates to measuring of the seal or lamination strength between the same or different web materials, particularly thermoplastic materials that may be heat sealed or laminated together, by pulling apart the sealed strips of the webs and measuring the force required to do so. It further relates to testing of the hot tack properties of such materials. "Hot tack" is the expression for the strength of heat seals subsequent to heat seal formation but prior to cooling of the seal to ambient conditions at which it has achieved its full strength, typically referred to as "seal strength." Information on hot tack properties is of interest to manufacturers and users of basic polymers, plastic films and laminates.

Hot tack properties are of particular importance in respect to so-called "form and fill" machines which create from film a continuous stream of packages closed by film-to-film seals which are filled with a product while a bottom seal is being made on each package by heat seal dies that apply heat and pressure. Heat sealed closures are made very rapidly and it is important that the film create a sufficiently high tack, or adhesiveness, quite quickly as the seal cools after it has been made and the heat seal dies removed. This is so that the package can be quickly filled without destruction of the seal by the weight of the product. That in turn permits the heat seal dies to be quickly moved on to the next seal.

Although few are designed or adapted for determining hot tack properties, the many seal strength testers have been proposed in the past for measuring various cold adhesive and/or heat activated adhesive seals, some with automation of functions and/or control of various sealing and testing variables. Typically, as in the case of the laminate bond tester described in U.S. Pat. No. 3,580,065, free ends of laminated strips are pulled apart at a uniform rate since the velocity of delamination is an independent variable that must be maintain the same between tests in order for the parting force measured to be comparable. In some cases for testers utilized for testing full seal strength, such as in U.S. Pat. Nos. 3,850,033, 4,637,252 and 4,893,513, the force is measured and recorded over the time that delamination of the seal proceeds, i.e. as a function of time. The maximum force thus recorded is taken as the delamination force. Alternatively this data is integrated to arrive at the energy value representing the energy required to delaminate the entire seal area.

In the case of the tester described in U.S. Pat. No. 4,958,521, the free ends of the laminate are pulled linearly in opposed directions at the same speed such that the line of delamination of the test strip remains essentially at the same position. This permits a guide roller adjacent this position to maintain the test strip at a desired angle as it approaches the location of delamination.

Various testers, such as those of U.S. Pat. Nos. 3,548,652, 3,850,033 and 4,637,252, and DDR Patent Publication 142756 laid open Jul. 9, 1980, are equipped to automatically first create seals or laminations of test strips under controlled conditions and then pull them apart and measure the force required.

The testers of U.S. Pat. Nos. 3,580,065 and 5,144,845 and Russian Patent 1259 157 A describe adhesion strength test procedures in which the temperature of the sample to be tested can be adjusted to a desired value. In the case of the Russian patent, the sample strip is coiled around a heated roller so that a temperature gradient is established along the strip. The sample is then pulled apart as it is unwound, beginning from the outside end of the coil and the delamination force measured as delamination proceeds to the gradually hotter material toward the inside end of the coil. In this fashion the delamination force can be determined for the sample at different temperatures.

A few testers, such as the DTC Hot Tack tester sold by Topwave Instruments Oy and the tester described in DDR Patent Publication 142756, are designed specifically for testing heat seals and which first create such heat seals. In the DTC Hot Tack tester, a test strip of film is folded or lapped on itself and an area of the overlapped film is then subjected to heat and pressure by heat seal dies at prescribed temperature and time conditions to create a heat seal. The dies are then opened to release the film and either immediately or after a set delay time the two free ends of the overlapped strip are rapidly pulled apart to break the seal, while measuring the pulling force. The maximum force measured is then taken as the hot tack strength of the film for the particular heat seal temperature and delay time (if any) utilized. These testers suffer the limitation that only a single force measurement (the maximum force measured) is taken for each sample for the particular heat seal dwell time and delay period selected and thus multiple tests would be required to measure the rate of gain of strength as the seal cools. Also, the rapid speed of peel propagation employed may not be representative of the conditions found in actual package sealing operations, as in form and fill machines. Cooling of the seal in these testers take place in an uncontrolled fashion, which leads to further imprecision in the test results. Additionally, while operation of these testers is automated to some degree, they are cumbersome in operation and require hand manipulation of a test sample for its insertion between the heat seal dies, thus making the operation susceptible to human error, particularly with inexperienced operators.

SUMMARY OF THE INVENTION

The invention relates to a method and apparatus capable of measuring the hot tack properties of a heat sealable material and which, in a single automated test, can measure seal strength over a range of temperatures of the seal as it is cooled over time following removal from the heat seal dies. In the method, a lapped portion of a test strip is inserted between heat seal dies and heat sealed. The strip is then removed from the heat seal dies to a position with the heat seal portion in a cooling zone in which the heat seal is cooled at a prescribed rate. While the seal remains in the cooling zone, the unsealed ends of the test strip are pulled slowly apart at a prescribed constant rate, preferably between 2 and 100 cm/minute and desirably below 400 cm/minute, and the force required to delaminate the seal is continuously captured and recorded as a function of time from removal from the heat seal dies, thus providing data on seal strength for a full range of temperatures of the heat seal as it cools over time.

Advantageously, the unsealed ends are pulled at the same rate so as to maintain the peel line of the remaining part of the seal at approximately the same location. In this way only a small cooling zone is required, concentrated in that location.

In a yet further feature of this invention, upon release of the heat sealed portion from the heat sealer, the ends of the strip are rapidly moved apart, desirably at a rate above 20 cm/second, to rapidly remove the sealed portion of the strip from between the heat seal dies to a zone of uniform cooling and to fully extended the strip with the heat sealed portion to one side of the strip in the uniform cooling zone. Then, the peeling process is initiated at a prescribed constant low rate of pull for delaminating the seal and measurement of the force required commenced.

This invention further relates to a procedure and apparatus that fully automatically inserts a test strip between heat seal dies after the test strip has been mounted in the tester and the test operation commenced. The ends of the test strip are each secured by the grippers that will be utilized to pull each end of the strip along a linear path to delaminate the heat seal. Heat seal dies are located midway along and to one side of the linear path of movement of the grippers. With the grippers in a retracted position there will be sufficient slack in the test strip so that it can be lapped upon itself and the lapped portion moved between the heat seal dies and be held in this position in a taut condition for heat sealing. To carry out this operation a threading bar is employed which has a path of movement from a starting position on the opposite side of the path of the grippers from the heat seal dies, through the opening between the dies and to a position to the other side of the dies. As the threading bar moves from its starting position it intercepts the strip intermediate its ends and pulls a portion through the opening between the dies and in doing so laps the portion of the strip pulled through the opening. The test strip is then liberated from the threading bar during the heat sealing operation, conveniently by cutting the strip at the threader. The strip is thus freed to move back out of the heat seal dies following sealing to then be pulled apart by the grippers.

DETAILED DESCRIPTION OF THE PREFERRED EMBODIMENT

The following description illustrates the manner in which the principles of the invention are applied but is not to be construed as limiting the scope of the invention.

Figure 1:
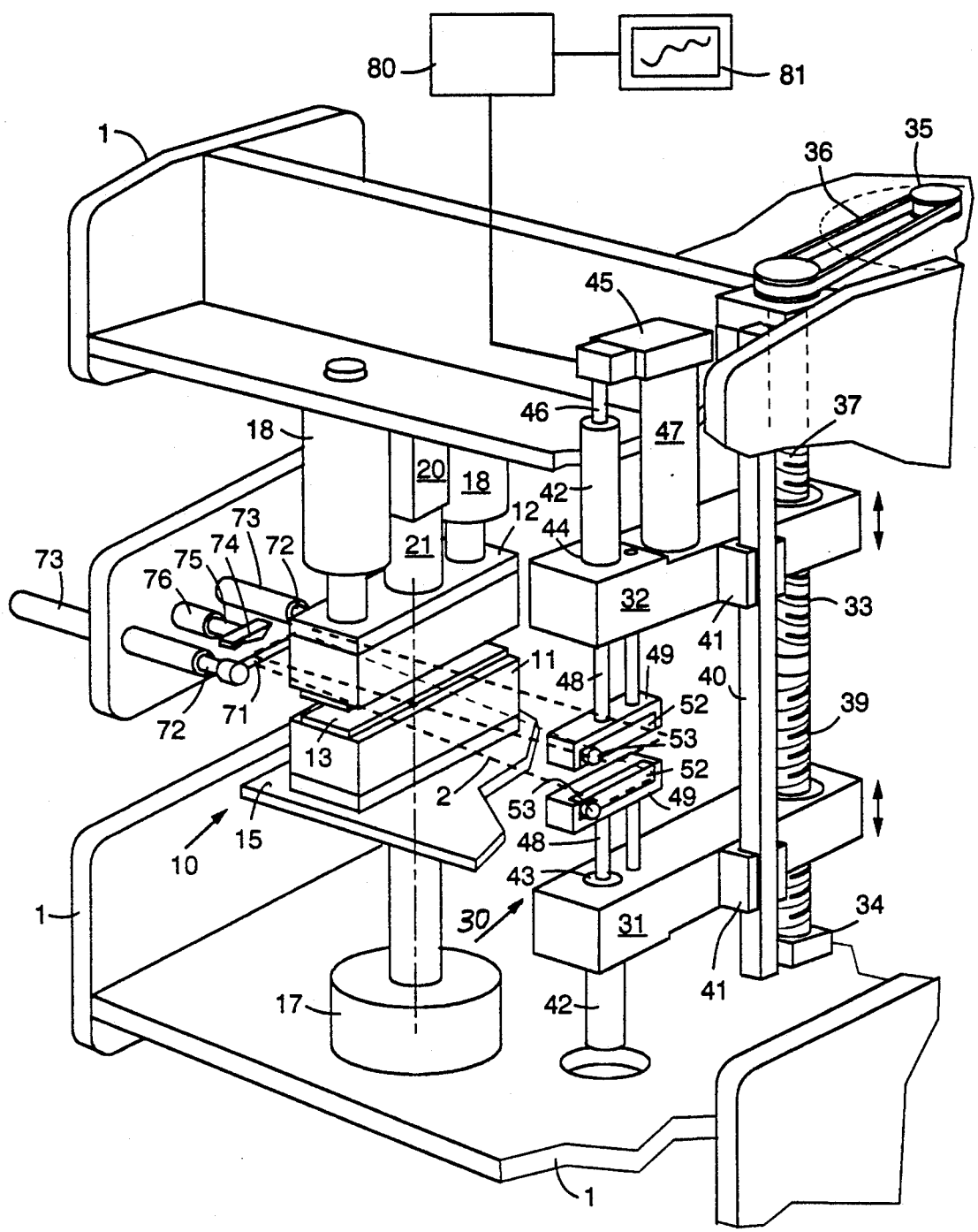
FIG. 1 is an isometric view of an embodiment of the hot tack tester of the present invention

Hot tack testing apparatus in accordance with this invention is shown generally in FIG. 1 of the drawings. A frame 1 supports the testing apparatus which includes a heat sealing unit generally indicated at 10 and a seal testing unit generally indicated at 30.

Figure 2:
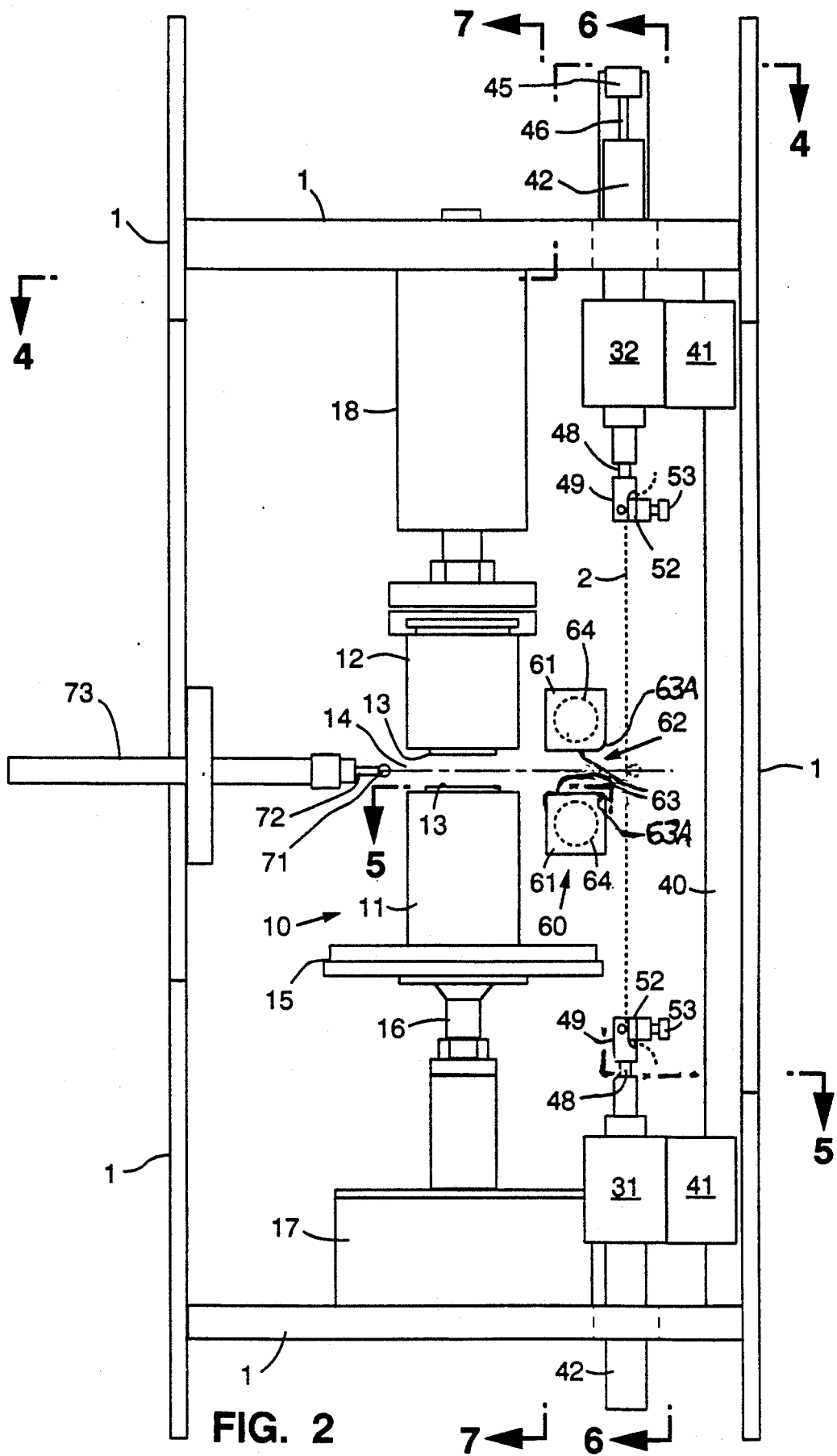
FIG. 2 is a front view of the apparatus of FIG. 1 in its operational mode at the inception of a test cycle with a test strip mounted for testing.
Figure 3:
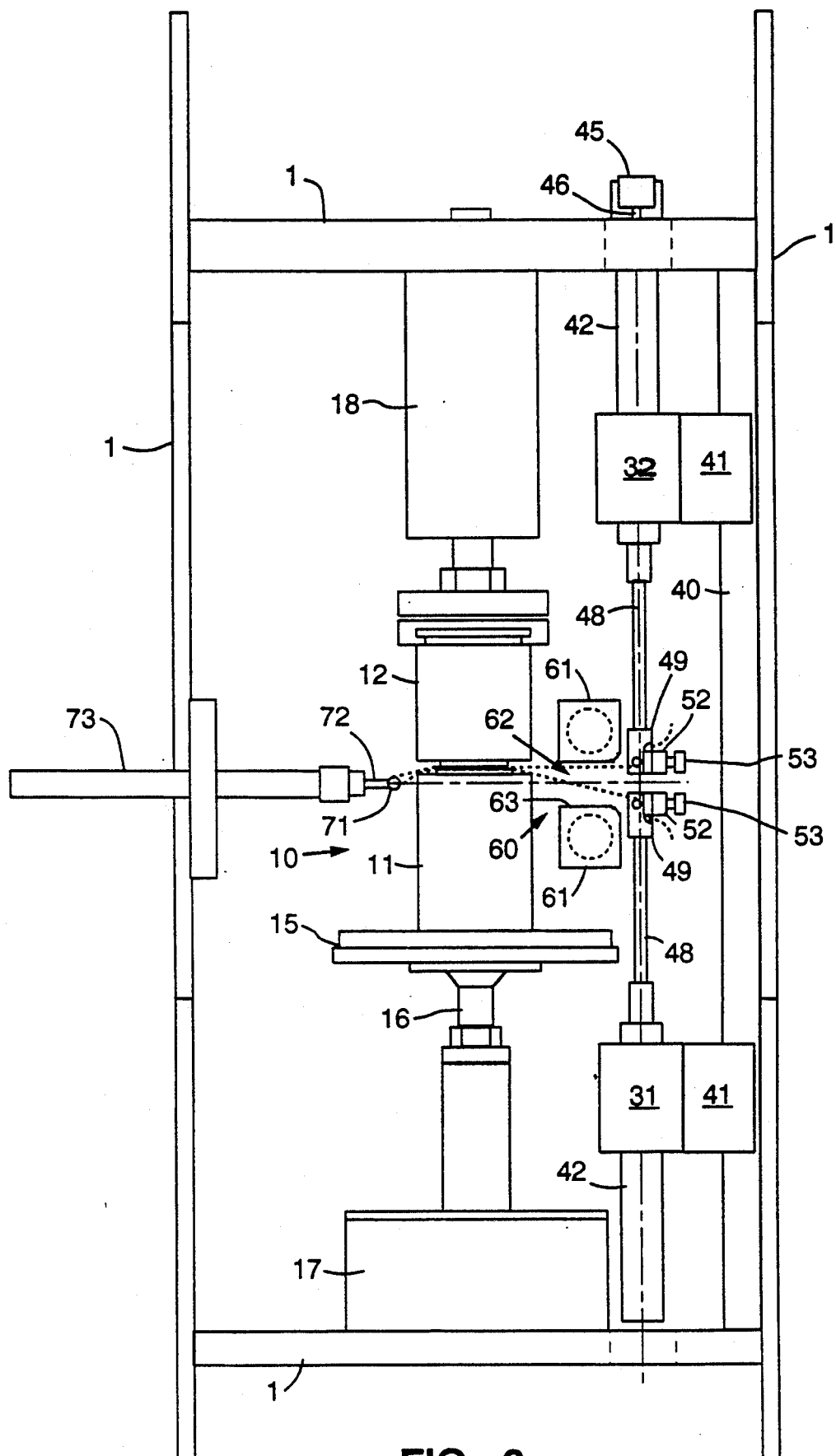
FIG. 3 is a is the same front view of FIG. 2 with the apparatus in its heat sealing mode with the test strip pulled between and engaged by the dies of the heat sealer.
Figure 7:
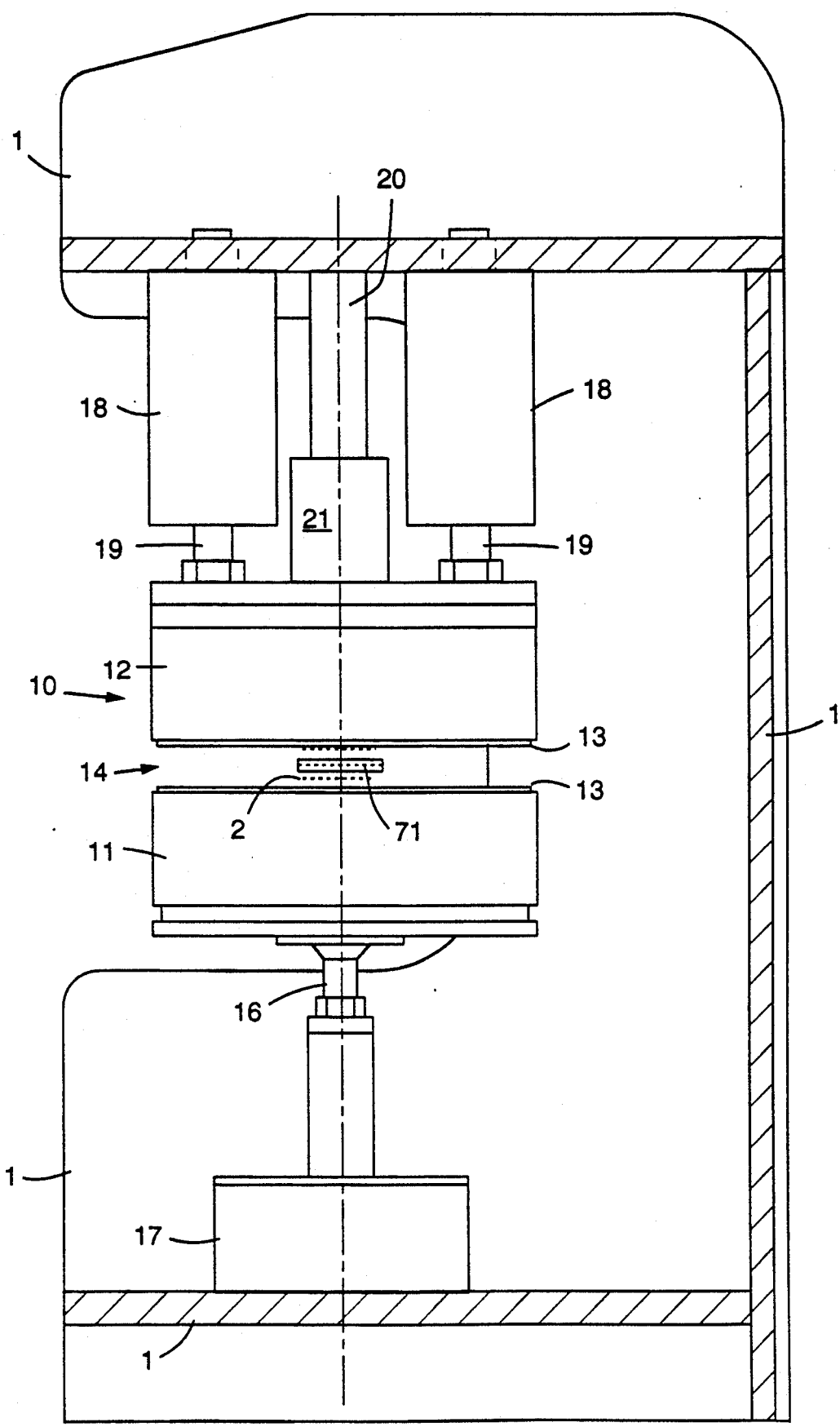
FIG. 7 is a sectional view taken along lines 7—7 of FIG. 2.

Referring particularly to FIGS. 2, 3 and 7, heat seal unit 10 is a conventional heat seal unit and is composed of a pair of opposed heat seal dies 11 and 12 each having an internal resistance heater (not shown) and provided with a flat, serrated or other surface 13 conventional to heat seal dies. Heat seal dies 11 and 12 are mounted for movement together to bring die surfaces 13 together to effect a heat seal and away from each other leave to gap 14 therebetween for threading a test strip between dies 11 and 12 and for removal of the heat sealed test strip. Specifically, heat seal die 11 is mounted on platform 15 which is mounted for free vertical movement. Platform 15 rests on the operating rod 16 of air cylinder 17 which in turn is secured to frame 1.

Heat seal die 12 is held in place by a pair of bearing cylinders 18. Rod 19 of each bearing cylinder 18 is attached to die 12 and is free to move vertically upward in its bearing 18 but is constrained from downward movement below a limit level. Load cell 20 attached to frame 1 at its upper end confronts the top end of ram 21 mounted at the midpart of the top of die 12 at a vertical position slightly above the top of die 12 with rods 19 at their limit level for downward movement. With this arrangement when die 11 moves upwardly against it upon operation of air cylinder 17, die 12 freely moves upward to and is held against load cell 20 during the heat seal operation so that pressure can be applied by dies 11 and 12 against the test strip and, at the same time, the pressure applied can be measured by load cell 20.

As seen in FIGS. 1, and 4–6, seal testing unit 30 is comprised of carriage 31 and carriage 32, each mounted for vertical travel towards and away from each other. This is accomplished by a double threaded acme screw 33 mounted on frame 1 for rotation about a vertical axis through bearings 34. Rotation is effected by electrical motor 35, mounted on frame 1, through pulley system 36. Electric motor 35 is a conventional variable speed motor having constant speed settings for movement of carriages 31 and 32 apart in speed ranges that will be described.

An acme or other type of lead screw 33 is engaged by each of carriages 31 and 32 through internally threaded openings 33 therein to effect vertical movement of the carriages upon rotation of acme screw 33. Acme screw 33 has right hand threads 37 above its midpoint support 38 and left hand threads 39 below support 38 so that rotation of acme screw 33 in one direction moves carriages 31 and 32 together and in the other direction moves them apart. Vertical guide rail 40 fixed to frame 1 is slideably engaged by each of carriages 31 and 32 through linear bearings 41 on each carriage.

Mounted on each of carriages 31 and 32 is an air cylinder 42. Air cylinder 42 on carriage 31 is fixed received by opening 43 therein. Air cylinder 42 on carriage 32 is slideably received by opening 44 therein and at its upper end is connected to load cell 45 through cable 46. Load cell 45 is mounted on pedestal 47, which in turn, is mounted on carriage 32.

Each of air cylinders 42 has an operating rod 48 each carrying a gripper 49. A guide rod 50 fixed to each gripper 49 is vertically slideably received by an opening through its respective carriage. Guide rods 50 eliminate rotation of the gripper about their operating rods 48. Air cylinders 42 are of such length that grippers are equidistant to the vertical gap 14 between dies 11 and 12 of heat seal unit 10 and, since carriages 31 and 32 move at the same rate, this relationship will be maintained throughout the movement of carriages 31 and 32. Also, operating rods 48 are of equal length such that when both are in either their extended or retracted position, grippers 49 are maintained equidistant to the vertical level of gap 14.

Grippers 49 each is comprised of a rectangular block containing a moving rectangular vise member 52 which closes upon a circular bar (not shown) by operation of thumb screw 53. Test strip 2 (seen in dotted outline) is inserted between the circular bar and vise member 52 and thumbscrew 53 operated to secure strip 2 therebetween.

Figure 5:
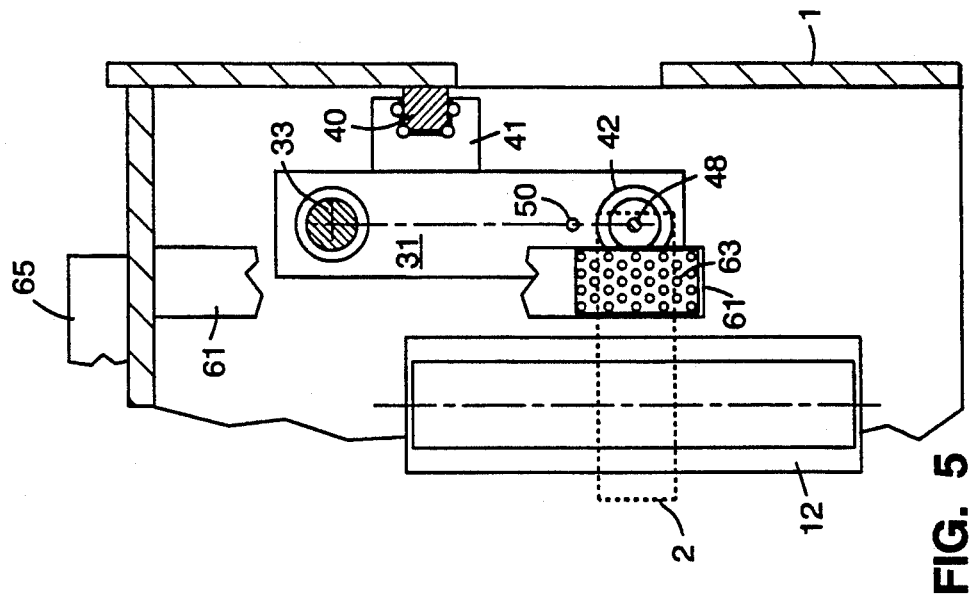
FIG. 5 is a partial sectional view taken along lines 5—5 of FIG. 2.
Figure 4:
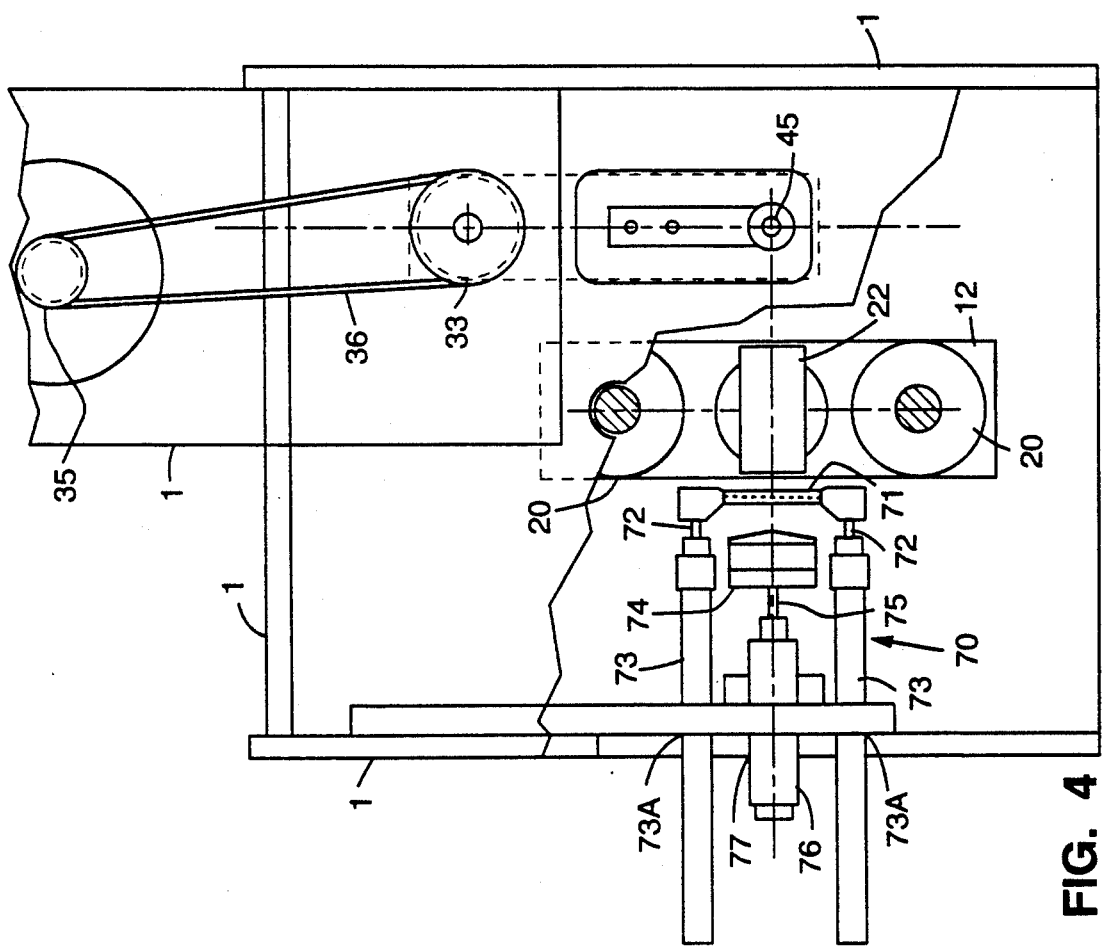
FIG. 4 is a top view of the apparatus of FIG. 1; with the top flange of the frame partially cut away.
Figure 6:
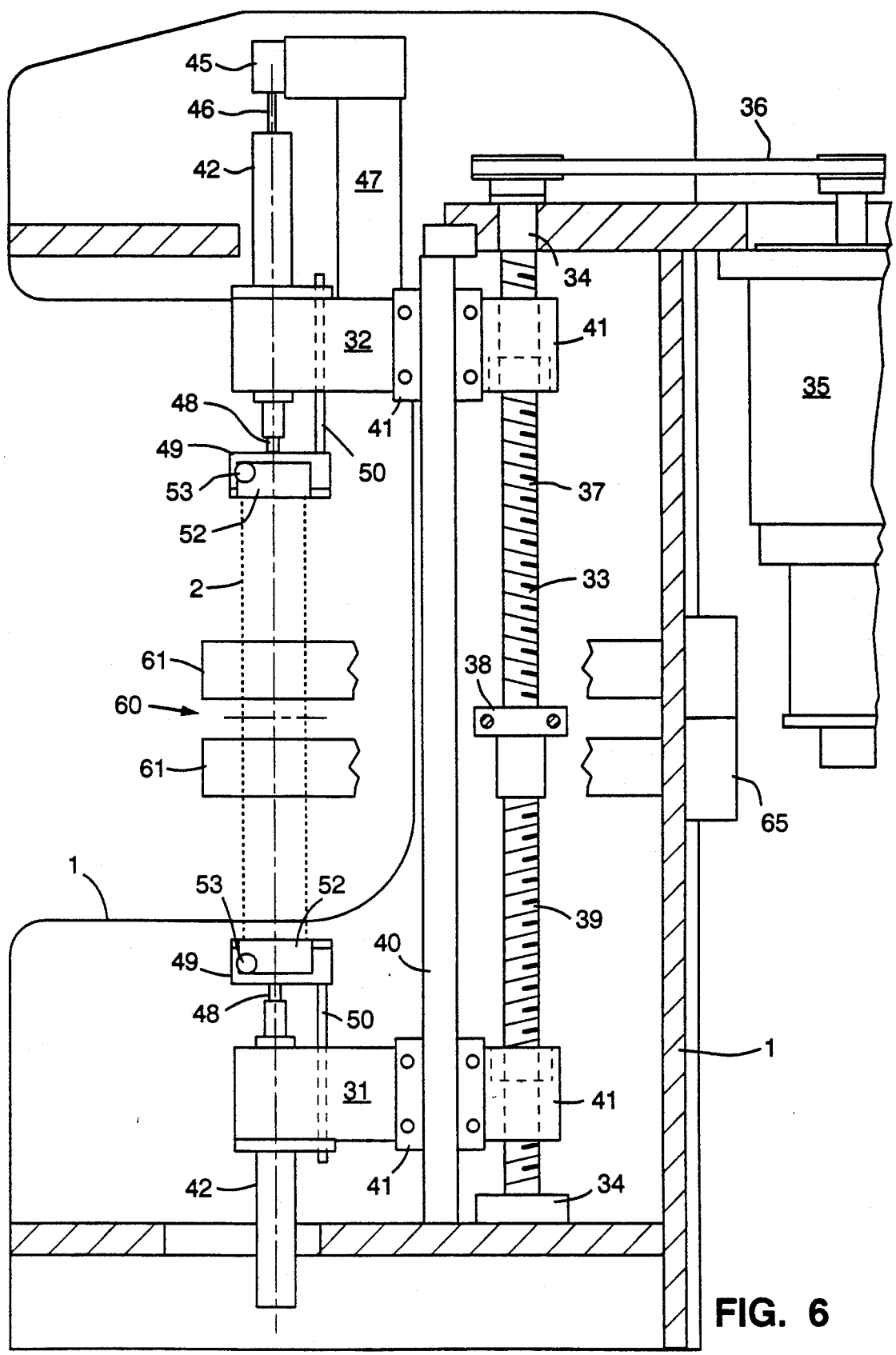
FIG. 6 is a sectional view of the apparatus of FIG. 2, taken along lines 6—6.

In FIGS. 2, 3 and 5 air conducting apparatus is shown generally at 60 and comprises a pair of spaced apart plenums 61 located adjacent the travel path of grippers 49 and between the travel path of grippers 49 and heat seal dies 11 and 12. One of plenums 61 is positioned, in the travel path direction of grippers 49, to one side of the midpoint between grippers 49 and the other plenum 61 to the other side of the midpoint. Plenums 61 are spaced apart to leave a gap 62 therebetween at the same vertical level as gap between dies 11 and 12 of heat seal unit 10 and centered on the midpoint between grippers 49. Gap 14 in the illustrated embodiment is approximately one-half inch wide. Plenums 61 in the illustrated embodiment are approximately 1 and ¼ inch wide in the direction of the of the travel path of a test strip 2 pulled through gap 14 of heat seal unit 10 (horizontally) and each plenum has an orifice 63 on their facing sides, comprising a 1 inch by 1 and ¼ inch rectangular metal screen. Orifices 63 are positioned such that one will fully overlie and the other fully underlie the sealed segment of test strip 1 when it is pulled from heat seal unit 10 and the test strip fully extended, as will be explained. Inner corner 63A along orifice 63 of each plenum 61 is rounded so that the sealed test strip does not ride against a sharp edge when it is pulled from the heat seal unit. Alternatively, a round bar (not shown) can be mounted along corners 63A to serve the same function.

Plenums 61 are each supplied with an air flow through a respective duct 64 (shown in dotted outline) each connected through holes in frame 1 to an air blower 65 mounted behind frame 1, so that air will flow from the duct through orifices 63 into gap 62. Preferably blowers 65 are sized to maintain a flow rate through each orifice 63 that will provide a positive pressure in the zone therebetween (gap 62) and sufficient to displace vagrant air currents, preferably a rate of one liter per second or greater.

Referring now to FIGS. 1-4, test strip threader unit is shown generally at 70. A threader bar 71 is transversely mounted on ends of operating rods 72 of a pair of air cylinders 73 which are fixedly engaged in holes 73A in frame 1 at the same vertical level as gaps 14 and 62. With operating rods 72 retracted, threader bar is positioned as shown in FIGS. 1, 3 and 8B-8D, on the opposite side of gap 14 from the travel path of grippers 49. With operating rods 72 in their extended positions, threader bar 71 is in the position shown in FIG. 8A, to the opposite side of the travel path of grippers 49 from heat seal unit 10. A strip cutter 74, located midway between operating rods and at the same vertical level, is mounted at the end of operating rod 75 of air cylinder 76 which is fixedly engaged in hole 77 in frame 1. Strip cutter 74, shown in retracted position in FIG. 1, upon activation extends horizontally to the location of threader bar 71 in its retracted position. Threader bar 71 has a longitudinal slot (not shown) which mates with strip cutter 74 when threader bar 71 is in the retracted position and strip cutter 74 is moved to the extended position. The sides of the slot act as shear surfaces so that strip 2 around threader bar is severed by strip cutter 74.

The operation of the air cylinder functions described are all controlled automatically by conventional means, preferably by computer control with a software program for appropriate synchronization for the operational sequences that will be described. As shown diagrammatically in FIG. 1, the electrical output of load cell 45 is connected to a computer 80 which is desirably set up (through wiring not shown) to monitor load cell 20 and appropriate temperature probes, including for heat seal dies 11 and 12 and air gap 62, the time elapsed during heat sealing and the time elapsed from opening of dies 11 and 12 after completion of heat sealing to the initiation of delamination and the time elapsed as delamination progresses. The analog data, including the output from load cell 45 is digitized in conventional fashion. Computer 80 is also programmed in a conventional fashion to register the delaminating force detected by load cell 20 against the time elapsed from release of the test strip from the heat sealer and to display this information in graphic form on monitor 81, as a plot of time from release of heat seal segment 3 from heat seal unit 10 on the abscissa against the force to delaminate on the ordinate. The various temperature and other readings from the test may also be displayed on the monitor. Additionally, if desired, the force data from the tester can simply be recorded at specific time intervals, to provide, for example, the times from release of the test strip from the heat sealer to a pulling force of 50 grams, 100 grams, 150 grams, etc. Other conventional modes of capture and retrieval of the force data can be employed. In a simpler embodiment the analog force data from the test can be fed to and registered on a conventional chart recorder.

Figure 8B:
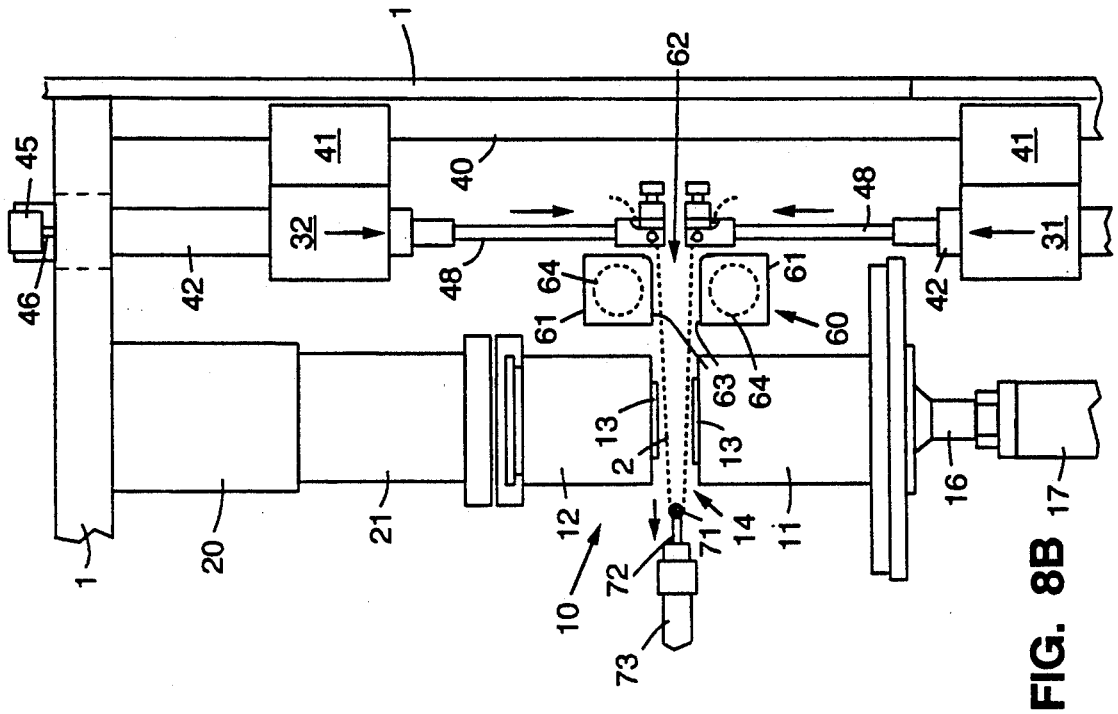
FIG. 8B is the fractional view of FIG. 8A with the apparatus in its operational mode with the test strip pulled between the heat seal dies in preparation for heat sealing of the strip.
Figure 8A:
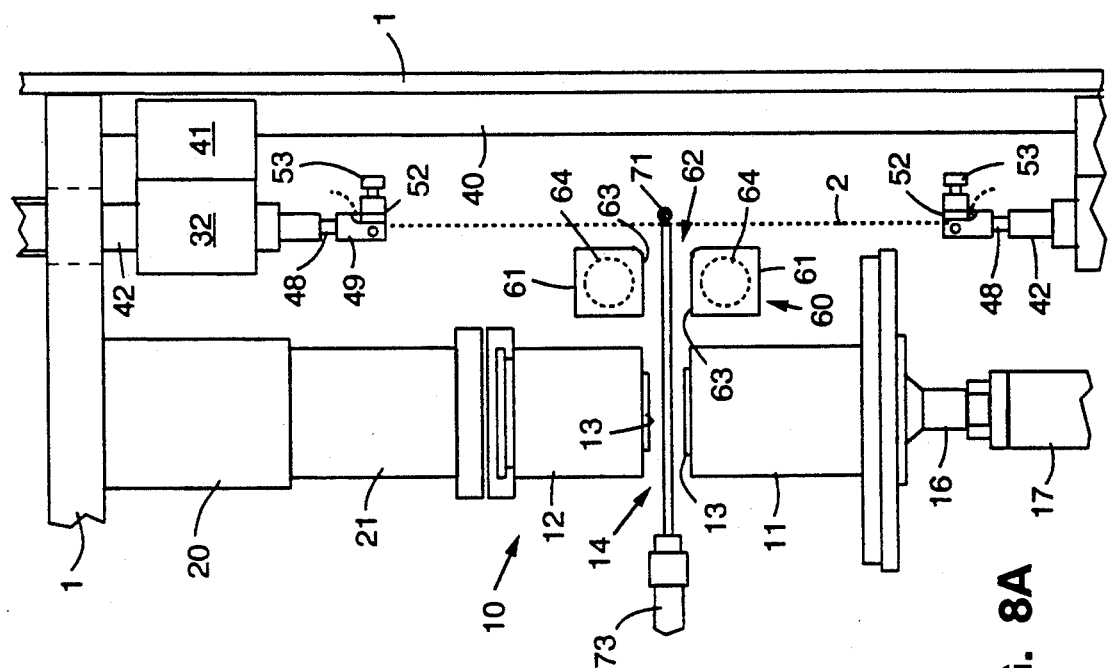
FIG. 8A is a fractional portion of the front view of FIG. 2.

In operation of the heat seal tester described, the testing cycle begins with the tester in the mode shown in FIGS. 2 and 8A with grippers 49 apart to receive a test strip 2 in extended condition. In that mode operating rods 72 of air cylinders 73 are extended so as to position threading bar 71 to the opposite side of the travel path of grippers 49 from heat seal unit 10. This consequently positions threader bar 71 to the opposite side of a test strip mounted on grippers 49 from heat seal unit 10 as the test strip extends along the path of travel of grippers 49.

A test strip 2 is manually mounted between grippers 49 and the automatic test cycle initiated by the operator. In the first step of the cycle air cylinders 73 are activated to retract operating rods 72 and thereby move threader bar horizontally through gaps 62 and 14 to the fully retracted position. As threading bar 71 moves horizontally to the retracted position it engages test strip 2 and carries a section of it through gaps 62 and 14 in overlapped condition. At the same time air cylinders 42 are activated to the extended position and carriages 11 and 12 are moved closer together by operation of motor 35 driving acme screw 33 a distance that will accommodate overlapping and pulling of a section of test strip 2 through gaps 49 and 14 but still leave strip 1 taut for proper heat sealing. The operational mode described with this portion of the cycle completed is shown in FIG. 8B.

Figure 8D:
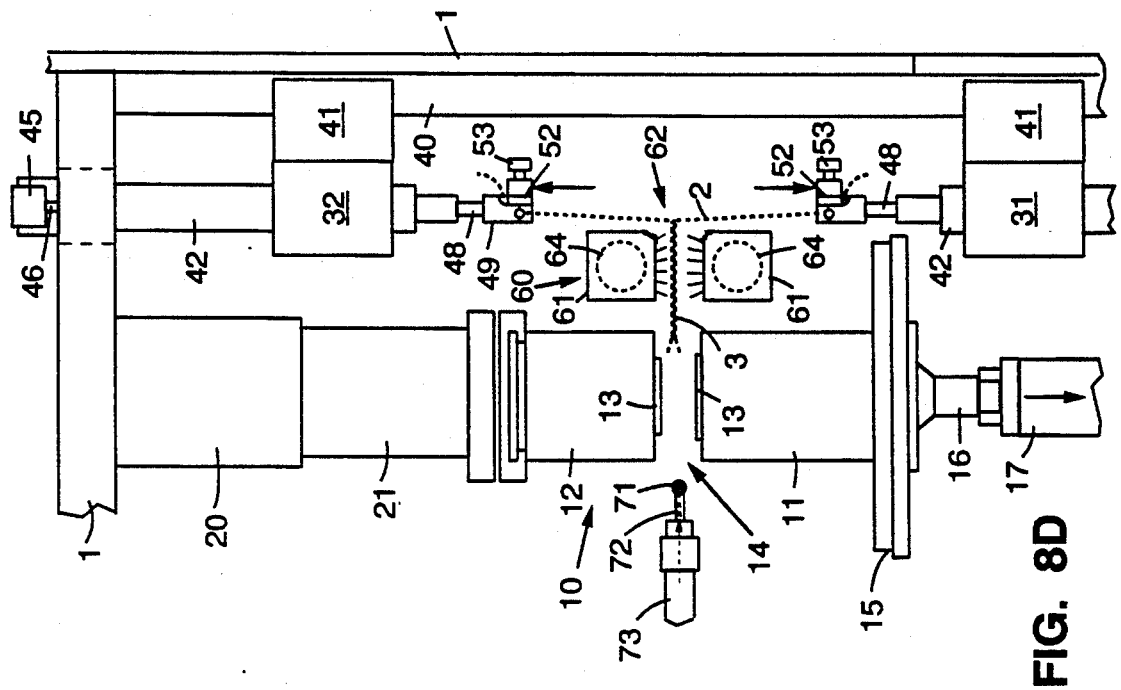
FIG. 8D is the fractional view of FIG. 8A with the apparatus in its operational mode with the test strip pulled from the heat seal dies after heat sealing and fully extended in preparation for delamination of the heat seal and FIG. 8E is the fractional view of FIG. 8A with the apparatus in its operational mode with the heat seal undergoing delamination and showing schematically equipment for force/time measurement, recording and display.
Figure 8C:
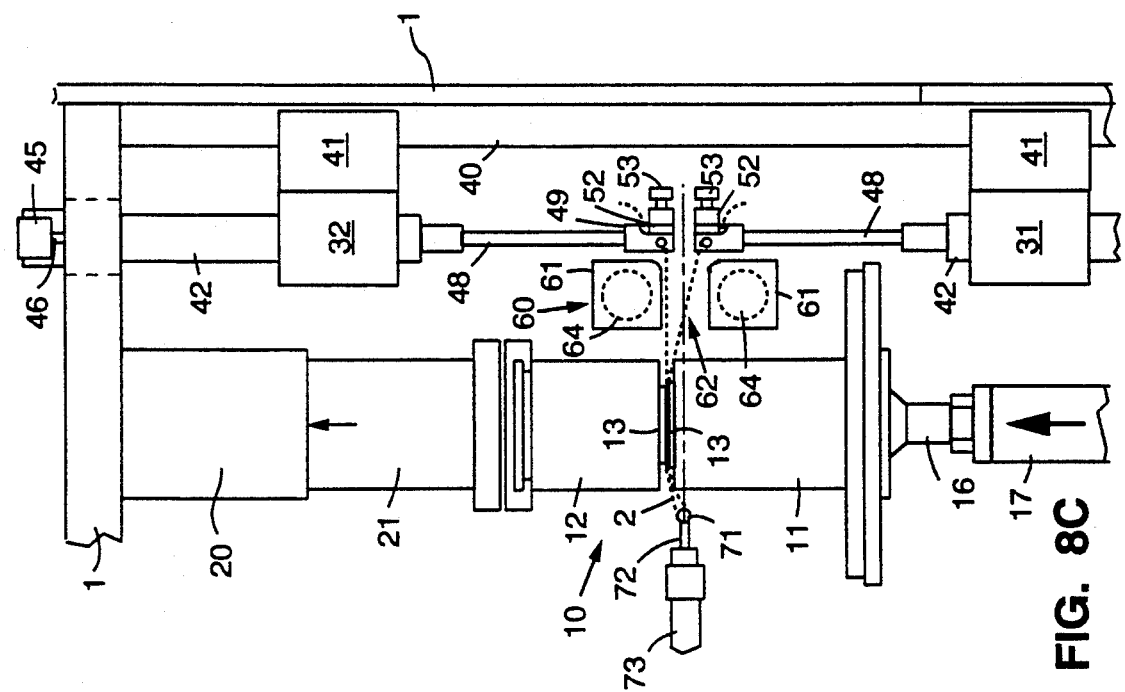
FIG. 8C is the fractional view of FIG. 8A with the apparatus in its operational mode with the test strip undergoing heat sealing.

Air cylinder 17 is then activated to close heat seal dies 11 and 12, which have been preheated prior to initiation of the cycle, and create a heat seal in a segment 3 of the overlapped section of strip 2, as shown in FIG. 8C. During the heat seal operation air cylinder 76 is activated to move strip cutter 74 through the slot in threader bar 71 to sever strip 2 extending around threader bar 71, using the slot as a shear member. This frees strip 2 from threader bar 71 for movement out of heat seal unit 10. At the end of the prescribed dwell time for the heat sealer, air cylinder 17 is activated to retract operating rod 16 and thus separate dies 11 and 12, to reopen gap 14. At the same time air cylinders 42 are activated to rapidly pull test strip 2 from heat seal gap 14 and to extend it along the path of travel of grippers 49, leaving the heat sealed segment 3 of strip 2 positioned in gap 62. The operational mode described with this portion of the cycle completed is shown in FIG. 8D.

Figure 8E:
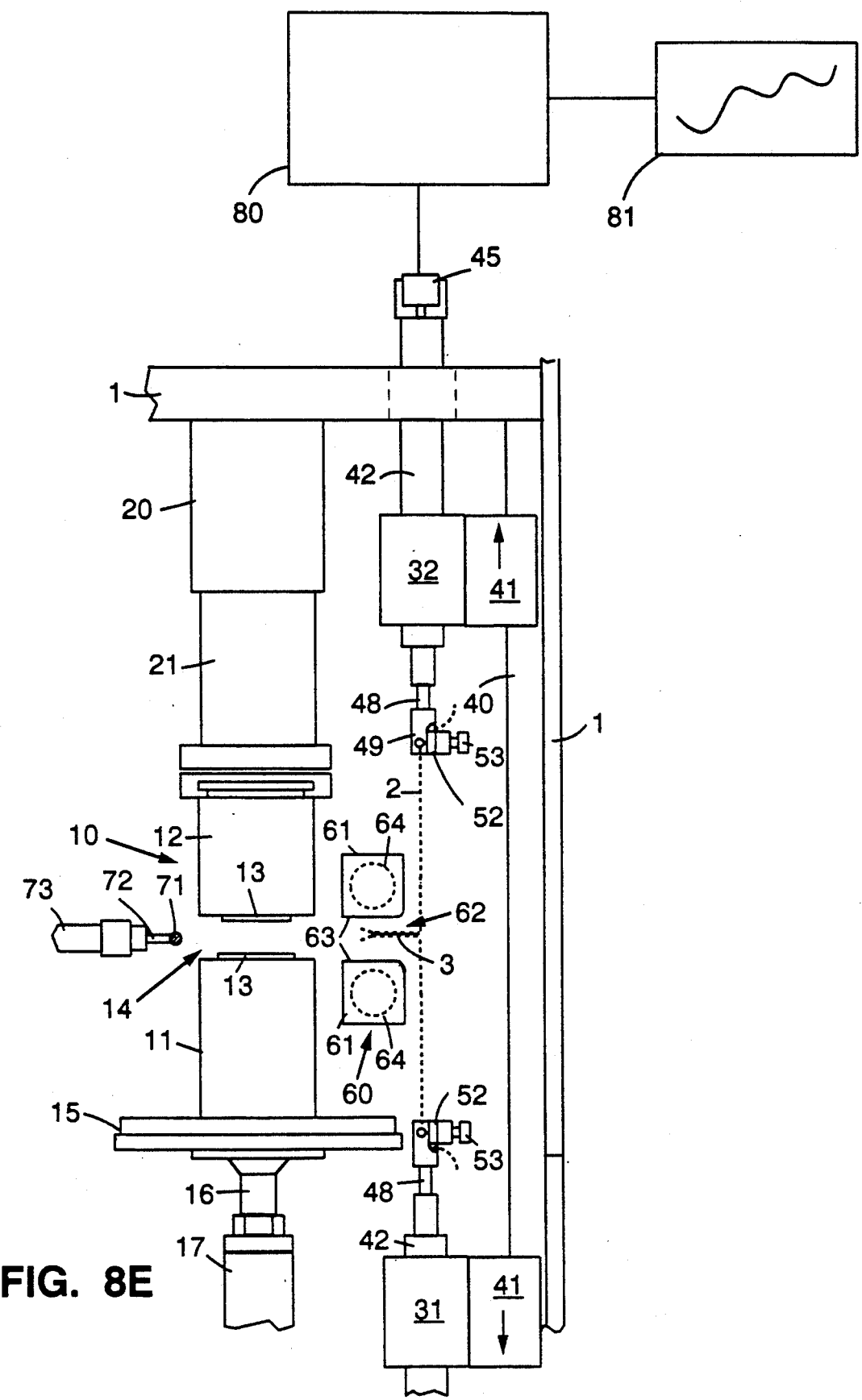

Progressive delamination of heat sealed segment 3 is then initiated by operation of motor 35 to move carriages 11 and 12, and hence grippers 49, apart to pull the ends of strip 2 at a prescribed appropriate constant speed for progressively delaminating segment, while measuring and recording the force applied (by load cell 45) as delamination progresses with time. The operation of this last portion of the cycle is shown in FIG. 8E. Following delamination of segment 3 the hot tack tester is returned to the operation mode for the beginning of a cycle.

Delamination is preferably carried out at the prescribed rate between of between 5 and 100 centimeters per minute as this is believed to most closely approximate the actual rate of tear propagation in heat seals in commercial packaging equipment, particularly in form and fill machines. Delamination rates of up to 400 centimeters per minute can be utilized in carrying out this invention but a progressively smaller portion of cooling time data will captured by a single test. To achieve these delamination rates in the apparatus described, variable speed motor 35, pulley system 36 and the threading of acme screw 33 are all selected so as to be capable of moving carriages 31 and 32, and hence grippers 49, at speeds throughout the range of 2 to 400 centimeters per minute.

For an ample amount of data from delamination over time, the heat seal segment will be at a length of 10 mm or greater, preferably one inch (or 25 mm). Delamination will generally extend for a period of 5 seconds to 10 seconds, depending upon the rate of pull. In the preferred range of about 5 to 100 cm/minute, the delamination period will typically extend about 12 to 30 seconds for a one inch heat seal segment. The width of the test strip for convenience and more reproducible results is the usual one inch (25 mm) for seal testing and the like.

Preferably, air cylinders 42 operate at a rate to move grippers 49 apart at a rate exceeding 20 cm/second and desirably 100 cm/second or higher so that there is minimum delay time between release of the strip from heat seal unit 10 and the inception of delamination. If desired, inception of delamination can be delayed for a short period after extension of test strip 2. Cooling of heat seal segment 3 will continue during this delay period so that the data produced will only be for the period of time from the later inception of delamination. When operating in the higher delamination speed range it may be necessary to make repeated tests in this fashion in order to obtain data over a longer cooling period.

Advantageously, the tester of this invention can also be used to test the seal after it has achieved full seal strength. This is accomplished by carrying out the test procedure as described, but utilizing a long delay period, for example 30 seconds to a minute, to permit cooling of heat sealed segment 3 to full strength development prior to initiation of delamination.

As is normal in good testing practice, and for the most reproducible results, testing in accordance with this invention is carried out in a controlled environment room with standard conditions (typically 72 degrees Fahrenheit and 50% relative humidity in the U.S.). Maintaining the heat sealed segment under constant cooling conditions during delamination as described is important to obtain the most accurate and reproducible results. Even in a controlled environment room the strip is still subject to temperature variations, particularly from convection currents and heat radiation, not only from sources outside the testing apparatus but also from the adjacent heat seal unit maintained at very high temperatures. Thus a constant stream of conditioned ambient air, preferably at a flow rate of one liter per second or greater, as described, will insure constant cooling conditions.

I claim:

1. A method of testing the hot tack properties of a strip of heat sealable material which comprises overlaying a portion of said strip with another portion of said strip, creating a heat seal on a segment of said overlaid portion by subjecting said segment to heat and pressure, removing the heat sealed segment from said heat and pressure, pulling apart said heat seal at a constant rate to progressively delaminate said heat seal, cooling said heat seal during said delamination and measuring and capturing for retrieval the pulling force on the strip with time as delamination progresses and wherein the ends of said strip are each affixed to a respective gripper prior to overlaying of said strip in opposed directions with said grippers positioned sufficiently close to each other to provide adequate slack in said strip for portions thereof to be overlaid for heat sealing, said grippers following heat sealing of said portions are moved rapidly apart a distance to quickly move the heat sealed segment from said heat and pressure and take up the slack in said test strip and then said grippers are moved apart at a slower substantially constant rate to effect said progressive delamination of said seal.

2. A method as in claim 1 and wherein said grippers are first moved apart at a rate of at least 20 cm/second to remove the heat sealed segment from said heat and pressure and take up the slack in said test strip.

3. Apparatus for testing heat seal bonds comprising
   a. means for creating a heat seal in a segment of a lapped section of a test strip,
   b. means for pulling the ends of said test strip in opposed directions to first move the heat sealed segment from the heat seal creating means and to fully extended said strip and then further to progressively delaminate said heat seal,
   c. means for measuring the pulling force to delaminate said heat seal with time as the delamination progresses and capturing the measurements for retrieval and
   d. means for establishing a zone of substantially constant cooling conditions at the location of said heat sealed segment when said strip is fully extended for delamination of said segment comprising means for circulating a substantially constant flow of air at said segment location.

4. Apparatus as in claim 3 and wherein said flow circulating means comprises air flow ducting having at least one orifice facing said segment location and spaced therefrom in one path of travel direction and at least one orifice facing said segment location and spaced therefrom in the other path of travel direction, whereby to direct air flow at the opposed sides of said segment during delamination thereof.

5. Apparatus as in claim 4 and wherein said means for pulling the ends of said strip comprises a pair of spaced grippers and means for pulling said grippers in opposed directions in a path of travel at a substantially equal rate, whereby to maintain said heat seal segment in approximately the same position along said path of travel as delamination progresses.

6. Apparatus for testing heat seal bonds comprising
   a. means for creating a heat seal in a segment of a lapped section of a test strip,
   b. means for pulling the ends of said test strip in opposed directions to first move the heat sealed segment from the heat seal creating means and to fully extended said strip and then further to progressively delaminate said heat seal, said means for pulling the ends of the test strip in opposed directions including means for rapidly moving the heat sealed segment from the heat seal creating means and extending said strip to a fully extended position and means for then pulling the ends of the fully extended strip at lower constant rate of speed to progressively delaminate the seal, and
   c. means for measuring the pulling force to delaminate said heat seal with time as the delamination progresses and capturing the measurements for retrieval.

7. Apparatus as in claim 6 and wherein said means for pulling the ends of the test strip comprise a first carriage and a second carriage, means for moving said carriages apart at a constant rate along a travel path, a gripper mounted on each carriage for movement between an extended position along said travel path toward the other gripper and a retracted position along said travel path in the direction away from the other gripper and means for rapidly moving each of said grippers from an extended position to a retracted position.

8. Apparatus as in claim 6 and wherein said heat sealing means includes heat seal dies movable from an open position with a gap therebetween for receiving a sample for heat sealing to a closed position for heat sealing a sample and said means for pulling the ends of the test strip include a pair of spaced grippers to one side of said heat seal dies for holding the ends of the test strip during insertion of a portion thereof between the heat seal dies for heat sealing and subsequently for pulling the ends of said test strip in opposed directions along a travel path to first remove the strip from the heat seal dies and fully extended the strip and then to progressively delaminate said heat seal, said grippers being moveable to retracted positions with a spacing therebetween to provide slack in said strip for lapping and heat sealing a portion thereof.

9. Apparatus as in claim 8 and wherein said means for pulling the ends of said strip further comprises means for pulling said grippers in opposed directions in a path of travel at a substantially equal rate, whereby to maintain said heat seal segment in approximately the same position along said path of travel as delamination progresses.

10. Apparatus as in claim 9 and including means of establishing a zone of constant cooling conditions comprising a fan for directing air flow adjacent said path of travel at the position of said heat seal segment as delamination progresses.

11. Apparatus as in claim 8 and wherein said means for pulling the ends of the test strip further comprise a first carriage and a second carriage, means for moving said carriages apart at a constant rate along a travel path, one of the grippers being mounted on each carriage for movement between an extended position along said travel path toward the other gripper and a retracted position along said travel path in the direction away from the other gripper, and means for rapidly moving each gripper from the extended position the retracted position.

12. Apparatus for testing heat seal bonds comprising
   a. heat sealing means including heat seal dies movable from an open position with a gap therebetween for receiving a sample for heat sealing to a closed position for heat sealing a sample,
   b. means for mounting and holding a test strip for testing including a pair of spaced grippers to one side of said heat seal dies for holding the ends of the test strip during insertion of a portion thereof between the heat seal dies for heat sealing and subsequently for pulling the ends of said test strip in opposed directions along a travel path to first remove the strip from the heat seal dies and fully extended the strip and then to progressively delaminate said heat seal, said grippers having retracted positions with a spacing therebetween to provide slack in said sample for lapping and heat sealing a portion thereof,
   c. a threading bar having a first location on the opposite side of said travel path from said heat seal dies and being movable toward and through the gap between said heat seal dies to a second position on the other side of said heat seal dies, whereby to intercept a strip held by said grippers when said grippers are at said retracted positions and to pull through said gap a section of the strip in lapped condition for heat sealing and
   d. means for releasing said threading bar from said strip prior to removal of the heat sealed section from between the heat seal dies.

13. Apparatus for testing heat seal bonds as in claim 12 and wherein said means for releasing said threading bar from said strip comprises means for severing said strip at a location to said other side of said heat seal bars.

* * * * *